United States Patent [19]

Hanlon

[11] Patent Number: 4,478,215
[45] Date of Patent: Oct. 23, 1984

[54] BREATHING DEVICE

[76] Inventor: Raymond J. Hanlon, 4 Wildflower Rd., Barrington, R.I. 02806

[21] Appl. No.: 401,497

[22] Filed: Jul. 26, 1982

[51] Int. Cl.³ ............................................ A61M 15/00
[52] U.S. Cl. ........................... 128/201.13; 128/207.14
[58] Field of Search ...................... 128/201.13, 204.17, 128/265.29, 207.14; 165/46, DIG. 12; 55/DIG. 35

[56] References Cited

U.S. PATENT DOCUMENTS 3,326,214  6/1967  McCoy ........................... 128/201.13
3,548,823 12/1970  Bogacik ........................ 55/DIG. 35
3,814,094  6/1974  DeAngelis et al. ............ 128/201.13

FOREIGN PATENT DOCUMENTS 1434893 1/1969  Fed. Rep. of Germany ...................... 128/201.13

OTHER PUBLICATIONS

Air Trap Breathing Device, Observations on Applicant's Invention, Feb. 6, 1984.
Respiratory Function Impairment & Cardiopulmonary Consequences in Long-Time Residents of the Canadian Arctic, Schaefer et al., CMA Journal, Nov. 22, 1980, vol. 123, pp. 997–1004.
International Track Club, Hanlon Air Conditioner.

Primary Examiner—Henry J. Recla
Assistant Examiner—Karin M. Reichle

[57] ABSTRACT

A device for use by runners, joggers and the like for preheating and/or limiting the volume of air entering the user's lungs through the mouth. The device is constructed such that it is retained at least partially in the user's oral cavity and preferably may be substantially completely held therein. The device includes a body of elongated construction formed of suitable materials such as plastic and the like and having a hollow interior open at both ends thereof. The hollow interior houses an open mesh element.

8 Claims, 5 Drawing Figures

BREATHING DEVICE

BACKGROUND AND OBJECTS OF THE INVENTION

This invention relates generally to a breathing device which is particularly suited to preheat incoming breath air through the mouth when the weather is cold. The device is also particularly suited to limit the volume of air entering the user's lungs through the oral cavity. As such, the device has utility for those working outside in cold weather as well as runners, joggers, and the like including serious athletes dependent on the manner in which the device is used.

It is well known that the inhalation of cold and particularly cold, dry air can be both uncomfortable and a source of irritation to the upper respiratory track. This is particularly true when exercising such as running, jogging and the like in temperatures which are particularly cold, i.e., at 0° F. or below. The effect of breathing such cold air at −20° F. can result in lung function impairment, overexertion of the heart and other detrimental effects such as those referred to by Dr. O. Schaefer in his article entitled "Respiratory Function Impairment and Cario-pulminary Consequences in Long-time Residents of the Canadian Arctic" CMA Journal, Nov. 22, 1980 Volume, page 123,997. A copy of such article is attached to this specification and is incorporated herein by a specific reference as an indication of the type of physical consequences from breathing cold air which can be avoided by the use of the present invention.

The present invention utilizes the concept of preheating the user's incoming breath by the residual heat and humidity supplied by the previous exhaled breath imparted to an open mesh element positioned in the device. Although such general concept has been known for some time, prior devices utilizing such concept have either been too cumbersome or complicated for simple use. Thus, the need remains for a device of an uncomplicated, simple, low cost nature which can be used by both amateur and serious athletes as an assist in their running or jogging efforts. Examples of previously known devices include those described in U.S. Pat. No. 3,326,214 issued June 20, 1967; U.S. Pat. No. 4,196,723 issued Apr. 8, 1980; and U.S. Pat. No. 4,201,206 issued May 6, 1980.

In addition to preheating the incoming breath, it is desirable that a device of this general nature may be able to additionally or separately limit the volume of air entering the user's oral cavity. By so limiting air volume, work level or heart rate which a user such as a middle-aged jogger is functioning may be regulated. Also as in the case of gold medal athletes, an anerobic overload state of exhaustion necessary in some types of training activity may be created. The device of the present invention accomplishes these desirable features by the provision of an air trap breathing device adapted to be held in the user's mouth with a portion thereof protruding therefrom and including an elongated hollow body open at both ends thereof in which an open mesh element is disposed in the hollow interior such that air entering the device through the breathing process is preheated and/or limited in volume thereby.

Other objects, features and advantages of the invention shall become apparent as the description thereof proceeds when considered in connection with the accompanying illustrative drawing.

DESCRIPTION OF THE DRAWING

In the drawing which illustrates the best mode presently contemplated for carrying out the present invention.

DESCRIPTION OF THE INVENTION

Figure 1:
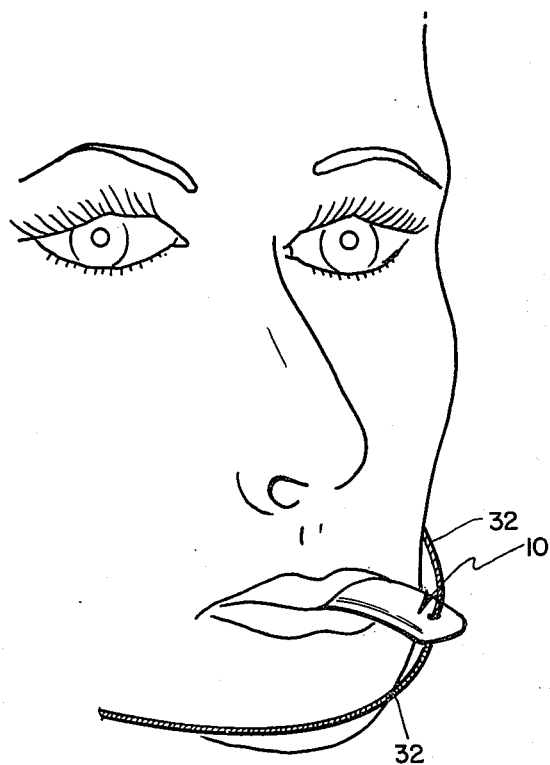
FIG. 1 is a perspective view of a user utilizing the device of the present invention, that is, gripping the base portion thereof in his or her teeth while permitting the remainder thereof to project through the lips.
Figure 2:
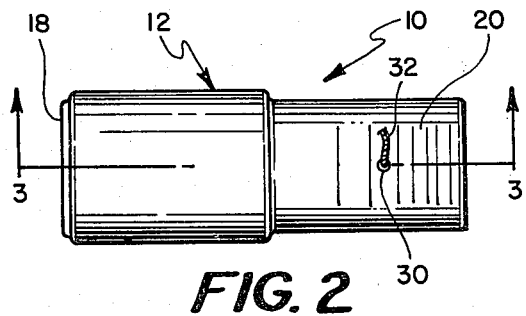
FIG. 2 is a top plan view of the device.

Turning now to the drawing, it may be apparent particularly from FIG. 1 thereof that the device 10 of the present invention may be conveniently held in the user's mouth. Such is in part facilitated by constructing the inner end 14 of the body 12 of the device of a heavier walled construction and in part by the flattened shape of such inner end. The body is normally constructed of a plastic material formed by conventional techniques such as blow molding. Suitable plastic materials include polyetylene and polypropylene which along with other polymeric materials provide a generally moderate insulative characteristic desirable in producing a satisfactory comfort level for devices of this type which are held in one's mouth.

The body of the device 10 is provided with a hollow continuous passageway 16 which opens at the inner end 14 in an open slot 18 and at the outer end 20 in a downwardly directed opening 22. The outer end 20 may be of less substantial construction, that is, a thinner walled construction and generally of lesser width and terminating in a downturned terminal portion such that the opening 22 when in the "use" position depicted is downwardly directed. An open mesh element generally formed from expanded aluminum and relatively closely packed together but permitting air to freely pass therethrough is positioned in the passage 16 generally within inner end 14. Such positioning serves the function that it enables the element 24 to maintain constant mouth cavity temperature, thus preventing water particles on the element from freezing in cold weather.

Thus it may be apparent that the device 10 of the present invention not only may heat the incoming air to the user's oral cavity by means of the heat residing in the element 24 by the previous exhaled breath but also that such element and the walls of the device 10 itself may be heated by conduction by its position in the mouth cavity. In other words, the user may run with the major portion of the device projecting from his or her lips or alternatively if a greater heating effect is desired, position the device such that only a small portion including the opening 22 projects from the user's lips.

In any event, the shape of the inner end 14 is such that the device can be comfortably held in the mouth, i.e., gripped by the teeth and positioned such that the outer end 10 projects therefrom. It is also desirable that the outer end project downwardly outwardly, that is, be of a curved nature such that moisture from the runner's mouth and nose may move along the outside of this portion of the device and drip off the end thereof. Also, it is advantageous that the opening 22 be cut or otherwise formed on a slant or bias such that a larger area opening is provided such that air may be brought in through the device and restricted only by the design, length, and openness of the element 24. When it is necessary to clear the element of excess moisture, the crook or curve in the outer end 20 thereof may naturally prevent the element 24 from being forced out the opening 22 when the user blows through the passageway 16 via the opening 18. The element may also be retained by stops (not shown) projecting into the passageway. It is also desirable that the inner end of the body be of a heavier weight construction so that it can be easily gripped in one's teeth and won't flatten so as to reduce the cross-sectional area of the passageway in that portion. Also, the inner end is preferably imperforate such that the user's saliva will not pass into the passageway except possibly through slot 18. When it is desired to clear the mouth saliva when utilizing the device, one's tongue can be forced into the slot 18 prior to the swallowing action and in this way a residual amount of saliva from the mouth cavity does not accummulate on the element thus undesirably restricting air flow through the element.

Figure 3:
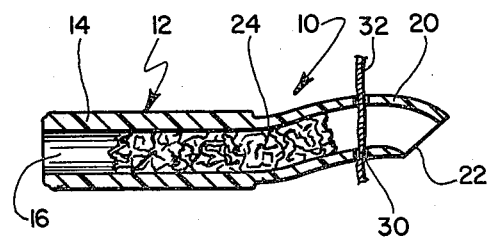
FIG. 3 is a sectional view taken along the line 3—3 of FIG. 2.
Figure 4:
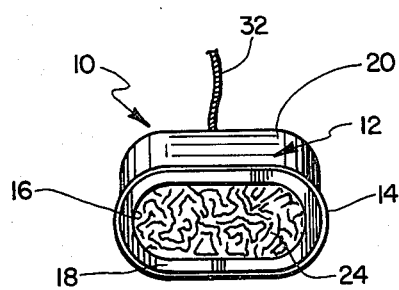
FIG. 4 is an end view thereof taken from the left-hand side of FIG. 2.
Figure 5:
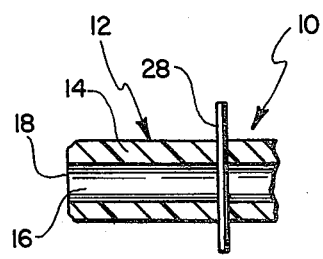
FIG. 5 is a sectional view similar to FIG. 3 but showing a modified form of the invention.

Specific provision for the prevention of swallowing the device may be provided. Turning now to FIG. 3, one such means is illustrated in the form of a safety line 32 threaded through an opening or bore 30 provided through the outer end 20 of the device. The line 32 is looped and adjustable in length so as to be worn around the user's neck. Another provision for the prevention of swallowing the device is shown in FIG. 5 in the form of a pin or rod 28 extending through the body.

Cleaning of the device so as to prevent odors, contamination, and the like may be provided by rinsing the device in cold running water before and after use. Also when not in use, the device may be stored in a container under a water solution of hypochlorite (approximately 1 part per 100 water). Also since water ph levels vary geographically, normal oxidation of the element may take place quicker in some regions than others. Therefore if the element loses its gloss or shine, it may be desirable to replace it. It may also be desirable to utilize disposable or at least easily replaceable elements and/or provide elements which vary the air intake limit through the device or which absorb less or greater amounts of heat depending on climatic and use conditions.

It may be thus seen that the device 10 of the present invention has maximum utility for a wide variety of uses. Thus the device has the potential to significantly preheat cold air masses inhaled through the mouth by athletes during cold weather training sessions so as to avoid upper respiratory irritation as previously described. In addition, the device has the potential to control the volume of air inhaled by weekend or middle-aged joggers so as to ensure that a runner keeps his or her heartbeat per minute during a workout at a level just below the recommended heartbeat rate. This allows a new or problem runner to read his or her body more carefully and minimize the chance of over-stressing his or her heart. The device also has use with professional or gold medal type athletes in that it allows such competitors to create anerobic overload states of exhaustion that surpass normal fatigue levels at sea level training conditions such that this overload conditioning process predisposes the body to adapt at higher stages of development both physiologically and psychologically. This overload concept of conditioning may be continued in warmer weather by elite athletes by simply removing the element from the passageway thus restricting the air flow by the passageway itself.

While there is thus shown and described herein certain specific structure embodying this invention, it will be clear to those skilled in the art that various modifications and rearrangements may be made without departing from the spirit and scope of the underlying inventive concept and that the same is not limited to the particular forms herein shown and described except to the extent indicated by the scope of the appended claims.

What is claimed is:

1. A breathing device for use by runners, joggers, and the like for preheating and/or controlling the volume of air entering the user's oral cavity through the breathing process, said device comprising an elongated hollow generally tubular body defining a flowpath therethrough having opposite inner and outer end portions terminating in open inner and outer ends, said inner end portion having a relatively thick wall construction with respect to said outer end portion and an oblong cross-section so as to facilitate gripping said inner end portion in the user's mouth by his or her teeth, said outer end portion adapted to extend between and beyond the user's lips so as to project at least partially out of said oral cavity, an open mesh relatively densely packed heat exchange element disposed in the flowpath of said body and acting as a moisture trap for exhaled air leaving said device and such that air entering said device is preheated and/or controlled in volume thereby, said inner end portion being straight and comprising substantially half of said tubular body, said outer end portion being curved and comprising substantially the other half of said tubular body whereby said tubular body can be easily maintained between a first position of at least partially to a second position of almost completely in the user's mouth and utilized as the only means by which air enters and exits the user's oral cavity 1 said heat exchange element disposed in said body such that it overlaps substantial portions of said inner and outer end portions wherein all of said heat exchange element within said body is positioned in said oral cavity in said second use position and a substantial portion of the heat exchange element is in said oral cavity in said first position such that said element is additionally heated by conduction by its position in said oral cavity in said first and second positions.

2. The device of claim 1, said inner and outer end portions having upper and lower surfaces, said outer end portion terminating in said open outer end which directs the flow of gas in a downward direction with respect to said inner end portion.

3. The device of claim 2, including means for retaining said heat exchange element in said body such that it will not be accidentally dislodged therefrom.

4. The device of claim 3, said curved outer end portion being adapted to limit the longitudinal movement of said element within said body.

5. The device of claim 1, said element being a metallic mesh heat exchange element whereby the air entering the device is preheated by the residual heat passed on to said heat exchange element by the previously exhaled air.

6. The device of claim 4, said inner and outer end portions having upper and lower surfaces, said outer end portion terminating in said open outer end which directs the flow of gas in a downward direction with respect to said inner end portion.

7. The device of claim 1 or 4, said body including means for preventing the device from completely entering the oral cavity adjacent said open outer end so as to prevent the device from being swallowed.

8. The device of claims 1 or 4, said heat exchange element being replaceable.

* * * * *